US011260563B2

(12) United States Patent
Bacchereti et al.

(10) Patent No.: US 11,260,563 B2
(45) Date of Patent: *Mar. 1, 2022

(54) APPARATUS AND METHOD FOR PRODUCING A BIOCOMPATIBLE THREE-DIMENSIONAL OBJECT

(71) Applicant: S.M. Scienzia Machinale S.R.L., Cascina (IT)

(72) Inventors: Marco Bacchereti, Cascina (IT); Luca Bosio, Pisa (IT); Giorgio Soldani, Massa (IT)

(73) Assignee: S.M. Scienzia Machinale SRL, Cascina (IT)

( * ) Notice: Subject to any disclaimer, the term of this patent is extended or adjusted under 35 U.S.C. 154(b) by 766 days.

This patent is subject to a terminal disclaimer.

(21) Appl. No.: 14/838,205

(22) Filed: Aug. 27, 2015

(65) Prior Publication Data

US 2015/0367542 A1 Dec. 24, 2015

Related U.S. Application Data

(63) Continuation of application No. PCT/IB2014/059291, filed on Feb. 27, 2014.

(30) Foreign Application Priority Data

Mar. 7, 2013 (IT) ................ PI2013A0015

(51) Int. Cl.
*B29C 41/36* (2006.01)
*B29C 41/08* (2006.01)
(Continued)

(52) U.S. Cl.
CPC ........... *B29C 41/365* (2013.01); *A61F 2/062* (2013.01); *A61F 2/2481* (2013.01); *B29C 41/08* (2013.01);
(Continued)

(58) Field of Classification Search
None
See application file for complete search history.

(56) References Cited

U.S. PATENT DOCUMENTS 4,538,364 A * 9/1985 Jensen ............... B65D 88/72
34/170
5,376,117 A 12/1994 Pinchuk et al.
(Continued)

FOREIGN PATENT DOCUMENTS

JP H9-314305 A * 12/1997
JP 2006509658 3/2006
(Continued)

OTHER PUBLICATIONS

Pre-Appeal Report for Appeal No. 2019-015002 (and translation) in co-pending Japanese National Phase No. 2015-560819 (of PCT/IB2014/059291) dated Jan. 6, 2020.
(Continued)

*Primary Examiner* — Matthew J Daniels
*Assistant Examiner* — Mohammad M Ameen
(74) *Attorney, Agent, or Firm* — Steptoe & Johnson LLP; Robert Greenfeld (57) ABSTRACT

An apparatus for making a biocompatible three-dimensional object including at least one delivery unit arranged to deliver at least one biocompatible fluid substance towards a support body having a matrix surface to obtain a coating layer of a predetermined thickness configured for coating the matrix surface. Furthermore, a handling unit is provided arranged to provide a relative movement according to at least 3 degrees of freedom between the support body and each delivery unit. The support body is arranged to be coated by the delivered biocompatible fluid substance, in order to obtain a three-dimensional object having an object surface copying the matrix surface of the support body.

11 Claims, 5 Drawing Sheets

(51) Int. Cl.
*A61F 2/06* (2013.01)
*A61F 2/24* (2006.01)
*B29L 31/00* (2006.01)
*B29C 41/34* (2006.01)

(52) U.S. Cl.
CPC ...... *B29C 41/34* (2013.01); *B29K 2995/0056* (2013.01); *B29L 2031/7532* (2013.01)

(56) References Cited

U.S. PATENT DOCUMENTS

| | | | | |
|---|---|---|---|---|
| 6,581,437 | B2* | 6/2003 | Chrystall | A43D 999/00 73/7 |
| 2004/0123435 | A1* | 7/2004 | Soldani | B01D 67/0004 28/100 |
| 2007/0076197 | A1* | 4/2007 | Koga | G01N 21/94 356/237.3 |
| 2008/0233302 | A1* | 9/2008 | Elsner | B29C 64/165 427/421.1 |
| 2013/0015596 | A1* | 1/2013 | Mozeika | B25J 9/0084 264/40.1 |
| 2013/0052291 | A1* | 2/2013 | Morikawa | B29C 64/153 425/135 |

FOREIGN PATENT DOCUMENTS

| | | |
|---|---|---|
| JP | 2012-236125 | 6/2012 |
| WO | 2002045933 | 6/2002 |
| WO | 2010059834 | 5/2010 |
| WO | 2010136983 | 12/2010 |
| WO | 2013019416 | 2/2013 |
| WO | 2014136021 | 9/2014 |

OTHER PUBLICATIONS

International Search Report and Written Opinion of the International Searching Authority in PCT Application No. PCT/IB2016/001377, dated Mar. 22, 2018.

* cited by examiner

APPARATUS AND METHOD FOR PRODUCING A BIOCOMPATIBLE THREE-DIMENSIONAL OBJECT

CROSS-REFERENCE TO RELATED APPLICATIONS

This application is a continuation of International Application No. PCT/IB2014/059291, filed Feb. 27, 2014, which claims priority to Italian Patent Application No. PI2013A000015, filed Mar. 7, 2013, each of which is incorporated by reference in its entirety.

FIELD

The present disclosure relates to an apparatus for making a biocompatible three-dimensional object with complex shape, i.e. made of two or more surfaces presenting different radius of curvature. In particular, the present disclosure relates to the production of tissues as well as biocompatible and blood-compatible membranes for making vascular prostheses, concave or convex heart patches, ellipsoidal cardiac chambers, patches for calcaneal ulcers, or other components of anatomical parts. The present disclosure relates also to a method for making such three-dimensional objects.

BACKGROUND

As well known, many techniques and apparatus exist for making tissues and biocompatible artificial membranes. In particular, the main known techniques provide the production of the above described artificial tissues by extrusion, or by spraying fluid substances. More in detail, the spraying techniques provide the deposit of a polymeric solution of synthetic origin by overlapping the polymeric solution in diluted form and a non-solvent, for example water, to each other. To this purpose a sprayer is used which sprays both substances in an alternated way, or, alternatively, two sprayers are used that deliver the two substances at the same time. The substances are deposited on a support body which has the same geometry of the desired tissue products or artificial membranes.

An example of an apparatus for making such membranes by spraying is disclosed in WO2004054775. The apparatus uses a plurality of sprayers, each of which draws from a respective reserve a component of the biological mixture. A cylindrical support element is then arranged on which the fluid substances supplied by the sprayers are deposited, in order to make a coating that forms the desired membranes. The cylindrical support element can kinematically rotate about a fixed rotation axis, whereas the sprayers are moved by a carriage that makes a translational movement along an axis that is substantially parallel to the rotation axis of the cylindrical support element. This way, the fluid substances supplied can deposit on the whole surface of the support element.

However, this solution, as it can be understood, is applicable only in case the membranes to make have a relatively simple and regular shape with surfaces presenting a wide radius of curvature and not too suddenly variable. Such membranes should also have substantially axisymmetric shape, in order to keep a constant spraying flow during the rotation of the support element.

A similar apparatus is disclosed in WO2010136983. Even in this case, the apparatus is used for making a biocompatible structure that allows regenerating biological tissues with simple shape. Notwithstanding the above, the apparatus as above described for making tissues or biocompatible artificial membranes cannot provide anatomical prostheses with complex shape, such as concave or convex heart patches, ellipsoidal cardiac chambers, patches for calcaneal ulcers, or portions of organs.

U.S. Pat. No. 5,376,117 describes a breast prosthesis for subcutaneous implants. The prosthesis consists of an outer shell comprising a non-porous layer of biocompatible polymeric material and a porous outer layer that coat wraps the non-porous layer. The outer layer is made by electrostatic deposit of biocompatible polymeric fibers on the inner layer. Once obtained the three-dimensional structure, the prosthesis is overturned and arranged on a spindle that is rotated about its own axis, in order to make the convex side of the prosthesis.

A breast prosthesis obtained by a process similar to that described in U.S. Pat. No. 5,376,117 is disclosed also in WO2010/059834. However, both processes, as described in U.S. Pat. No. 5,376,117 and WO2010/059834, are not suitable for the production of tissues and biocompatible artificial membranes with complex shape and with small tolerances, since they cannot ensure an accurate definition of the modelled forms.

SUMMARY

In general terms, the present disclosure provides an apparatus that allows the production of a biocompatible three-dimensional object with complex shape, i.e. not necessarily equipped with significant symmetries and, in particular with surfaces having different radius of curvature. The present disclosure may also provide an apparatus that allows for the production of such three-dimensional object with high dimensional precision, in order to copy accurately a pre-designed model.

Further, the present disclosure may provide an apparatus that allows programming the whole production work so that it can be carried out in an automatic way.

Briefly, and in general terms, the present disclosure is directed to an apparatus for making a biocompatible three-dimensional object. The apparatus includes at least one delivery unit arranged to deliver at least one biocompatible fluid substance towards a support body, also called core, that has a matrix surface, to obtain a coating layer of a predetermined thickness configured for coating the matrix surface. The biocompatible fluid substance may include a plurality of particles. The apparatus also includes a handling unit for determining a relative movement according to at least 3 degrees of freedom between the support body and the delivery unit. This is so that the support body may be coated with the delivered biocompatible fluid substance to obtain a three-dimensional object having an object surface copying the matrix surface of the support body. Further, the apparatus includes a suction and blowing unit is also provided configured to provide a suction and blowing current arranged to remove from the support body any surplus particles of the biocompatible fluid substance supplied by the or each delivery unit. In this example, it is possible to deposit a uniform predetermined thickness of coating layer on the matrix surface. The solution provided by the present disclosure, and in particular the possibility of actuating relatively the support body and the delivery unit according to at least 3 degrees of freedom during the coating steps of the matrix surface, makes it possible to control with high precision the deposit of the biocompatible fluid substance on the matrix surface. It is also possible to adjust, in a correspondingly precise way and as it is needed, the thickness of the layers of deposited fluid substance. This is possible since the handling unit is capable to expose the matrix surfaces of the support body to a jet of biocompatible fluid substance supplied by the delivery unit, positioning this matrix surface substantially orthogonally to the jet.

After the deposit of the fluid substances, the coating is removed from the support body giving rise to the sought three-dimensional object.

In certain embodiments, the handling unit is arranged to provide a relative movement according to 4 degrees of freedom, advantageously, according to 5 degrees of freedom, preferably according to 6 degrees of freedom. In one embodiment, the handling unit includes an anthropomorphic robot having a chain of pivot joints that has an end connected to a fixed base and the other end connected to a support base to which the support body, and/or the delivery unit, can be mounted in a removable way. Such chain of pivot joints is adapted to actuate the support body, and/or the delivery unit, according to at least 6 degrees of freedom, supplying higher design precision in generating the sought three-dimensional object.

Alternatively, the handling unit may include a plurality of actuators, each of which has one end engaged with a fixed base and another end engaged with a support base to which the support body, and/or the delivery unit, can be mounted in a removable way.

In certain embodiments, the actuators may be pneumatic actuators, hydraulic actuators, electric actuators, or a combination thereof.

In one embodiment, the suction and blowing unit may replaced with a suction device, or the suction and blowing unit may include a suction device and a blowing device. The suction device may be a fixed suction device. Alternatively, the suction device can be a movable suction device associated with auxiliary moving means arranged to move the suction device, in order to follow spatially the position of the support body during its handling by the handling unit. This way, any surplus particles of the biocompatible fluid substance can be removed regardless of the position of the support body.

In a further exemplary embodiment, the suction device may include a suction hood integral to the support base and configured to surround laterally the support body, in order to maximize the suction of any surplus particles of the biocompatible fluid substance. A suction tube may also be included which is arranged to connect pneumatically the suction hood with a suction system. This way, it is not necessary the implementation of the auxiliary moving means, since the hood is in an optimal position for suction of any surplus particles of the biocompatible fluid substance, whichever is the position of the support body. In one embodiment, the hood may have a toroidal, cylindrical, or tubular shape.

In one embodiment, the suction device may include a storage reservoir of any surplus particles or a filter on which such particles can deposit. Furthermore, the suction or blowing current from the suction and blowing unit can be generated by a fan or a compressor located upstream of the suction tube.

In one example, the apparatus may include a first delivery unit arranged to deliver a first jet of a first biocompatible fluid substance towards the support body. The first biocompatible fluid substance being a biomaterial of synthetic origin. The apparatus of this embodiment also may include a second delivery unit arranged to deliver a second jet of a second biocompatible fluid substance towards the support body. The second biocompatible fluid substance being a non-solvent, for example, water. The second delivery unit is arranged to direct the second delivery jet towards the support body, in order to overlap the second delivery jet to the first delivery jet. This may induce a quick deposit of the synthetic biomaterial supplied onto the support body by the first delivery unit, obtaining a filamentous three-dimensional structure.

In yet another embodiment, the apparatus also includes a counter-mold. The counter-mold may be adapted, once ended the delivery of the biocompatible fluid substances, to press, in particular to heat, the coating layer that is deposited on the support body. This is to obtain a better finishing of the shape of the three-dimensional object, in addition to improved mechanical features.

In another embodiment, the apparatus also includes third delivery unit arranged to deliver a third biocompatible fluid substance, in particular diluted in solution, both of synthetic and biological origin. In certain embodiments with two or three delivery units, with respective delivery of jets of biocompatible fluid substances, there may be a program means configured for combining the alternation of such delivery. This way, the step of coating can be completely automated, and does not require, in normal conditions, manual monitoring.

Also, in one embodiment, a control means is also provided for monitoring the thickness of the formed coating layer, in order to test that the coating layer has thickness corresponding to that of the designed coating layer. In particular, the designed coating layer can be provided to apparatus by a control CAD.

The current disclosure is also directed to a method for making a biocompatible three-dimensional object. The method includes the step of delivery of at least one biocompatible fluid substance towards a support body, also called core, which has a matrix surface. Also, the method includes obtaining a coating layer of predetermined thickness configured for coating the matrix surface. The delivery occurring using at least one delivery unit. The method also includes handling the support body and/or the delivery unit with a handling unit, in order to provide a relative movement according to at least 3 degrees of freedom between the support body and the delivery unit. This is so that the support body is coated with the delivered biocompatible fluid substance to obtain a three-dimensional object having an object surface copying the matrix surface. There may be multiple delivery units and the at least 3 degrees of freedom may be between the support body and each of the delivery units. The method also includes removing from the support body any surplus particles of the or each biocompatible fluid substance dispensed with a suction and blowing unit. The removing being carried out through a suction or a blowing step, in order to make uniform the predetermined thickness of the coating layer. The suction and blowing unit may be replaced with a suction device or a blowing device.

In one embodiment, the method includes pressing, in particular hot pressing, the coating layer that is deposited on the support body. This step of pressing is carried out at the end of the step of delivery of the fluid substance.

BRIEF DESCRIPTION OF THE DRAWINGS

The present disclosure will be now shown with the following description of some exemplary embodiments thereof, exemplifying but not limitative, with reference to the attached drawings in which.

DETAILED DESCRIPTION

Figure 1:
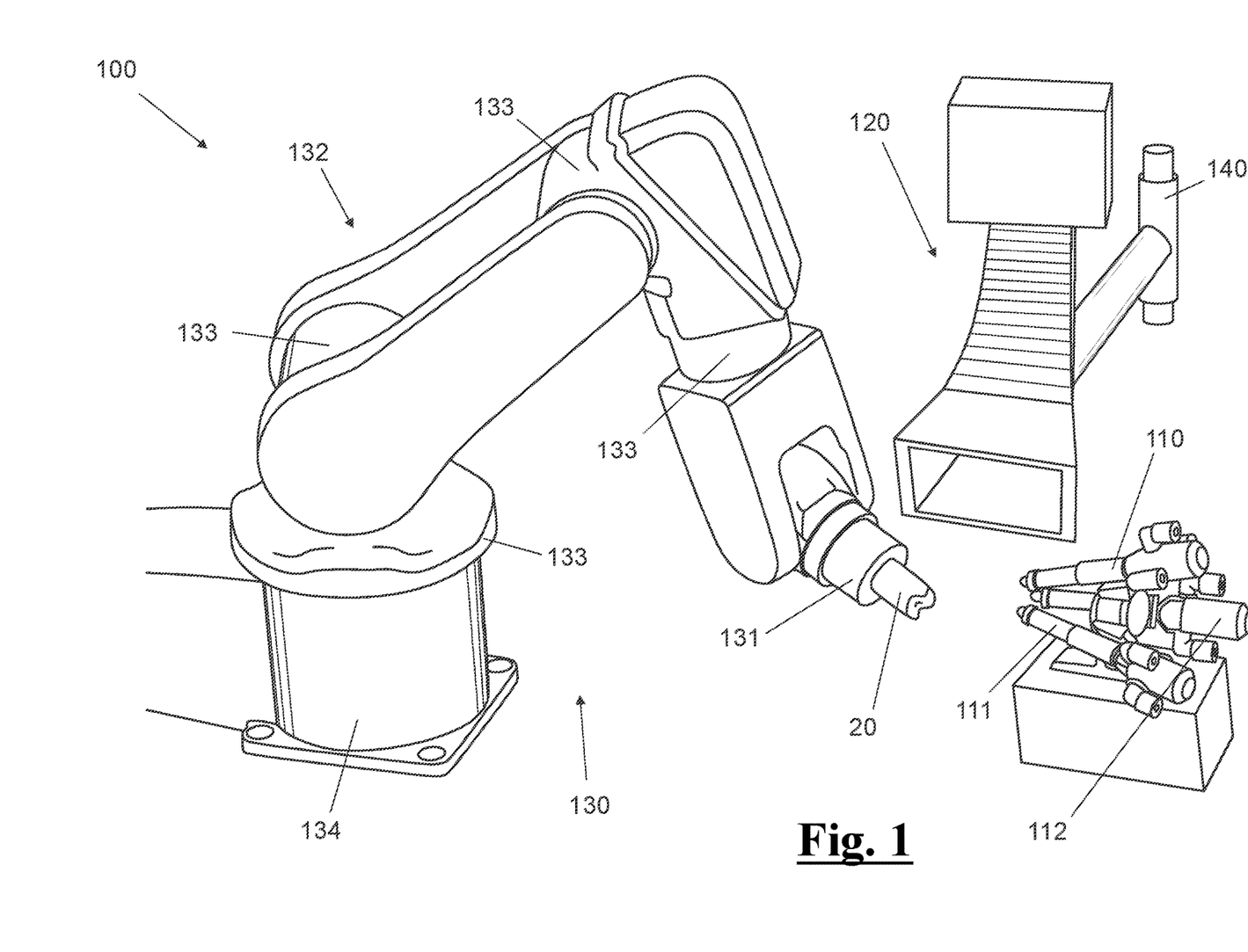
FIG. 1 shows an exemplary embodiment of an apparatus including an anthropomorphic robot arranged to handle the support body.

With reference to FIG. 1, an exemplary embodiment of an apparatus 100 for making a biocompatible three-dimensional object 30 provides an anthropomorphic robot 132 having a kinematical chain of pivot joints 133. Such chain of joints 133 is constrained at an end to a fixed base 134, and at another end to a support base 131 on which support body 20 engages in a removable way. The chain of pivot joints 133 of FIG. 1 allows handling the support body according to six degrees of freedom, allowing an optimum precision when generating the sought three-dimensional object 30.

In FIG. 1, three delivery units 110,111,112 are shown that are arranged to deliver three different biocompatible fluid substances. In particular, first delivery unit 110 is adapted to deliver a jet of a biomaterial of synthetic origin towards the support body 20. The second delivery unit 111 is, instead, arranged to deliver a jet of non-solvent, for example water, overlapping to the jet generated by first delivery unit 110, in order to induce a quick deposit of the biopolymeric material supplied onto support body 20 by first delivery unit 110, allowing to obtain a filamentous three-dimensional structure. The third delivery unit, finally, is adapted to deliver a third biocompatible fluid substance diluted in solution, in particular another biomaterial of synthetic or biological origin.

Each delivery unit 110,111,112 also has a hydraulic circuit (not shown in the figure, for example, a cylinder-piston mechanism) consisting of ducts, with possible valves and pumps, which connect the or each delivery unit to reservoirs containing the biocompatible fluid substances.

In this exemplary embodiment, a suction and/or blowing unit 120 is further provided, adapted to generate a suction and/or blowing current. This way, the suction and/or blowing unit 120 makes it possible to level the thickness of the coating layer 35 and to remove from support body 20 any surplus particles of the biocompatible fluid substances supplied by the or each delivery unit 110, 111, 112. The device 120 is also spatially moved by auxiliary moving means 140, in such a way that this device 120 can follow spatially the position of support body 20 during its handling steps by handling unit 130.

Figure 2:
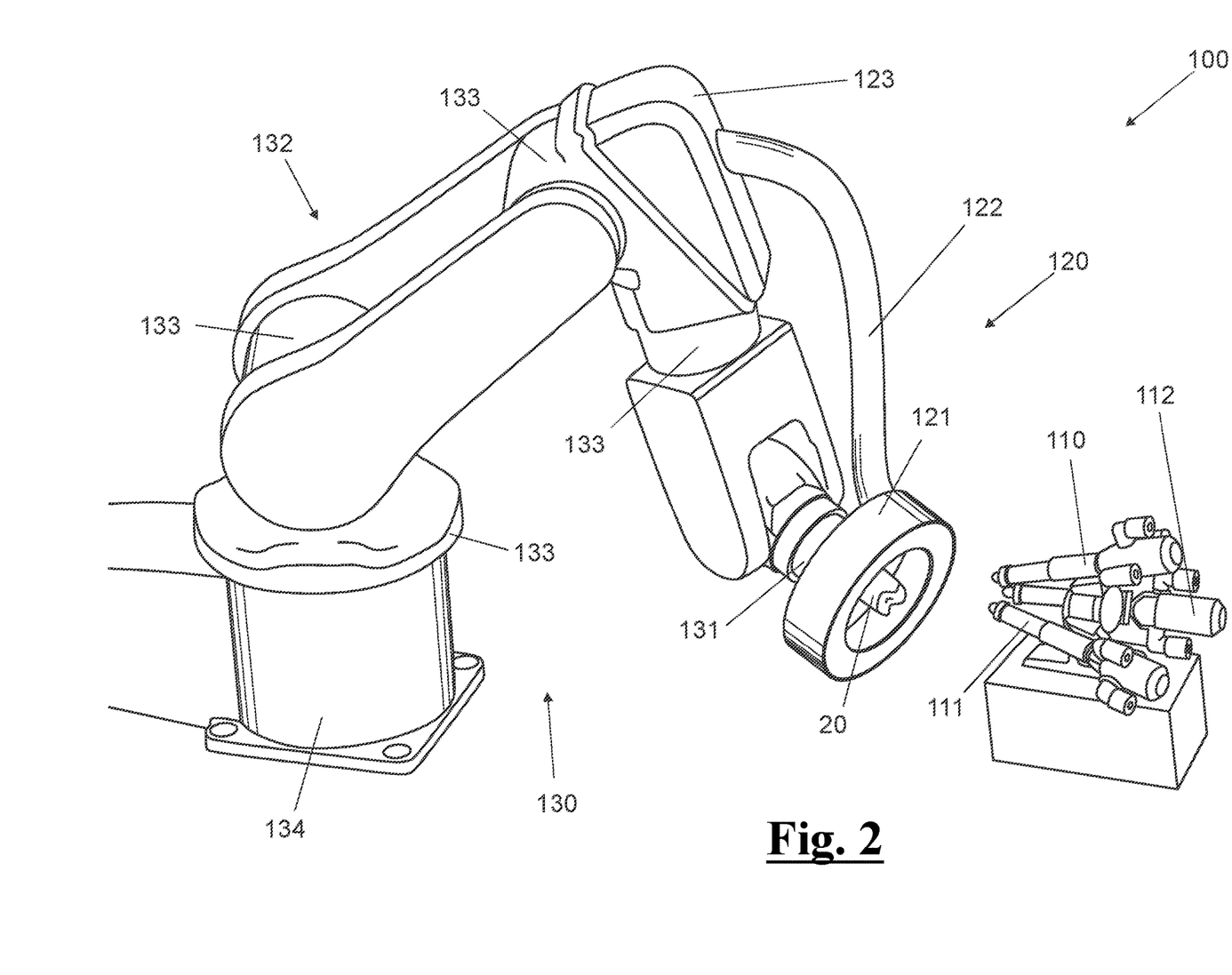
FIG. 2 shows an exemplary embodiment of an apparatus, which differs from that of FIG. 1 for the presence of a toroidal hood arranged to surround the support body.

In FIG. 2 a second exemplary embodiment is shown, which differs from an exemplary embodiment of FIG. 1 as from the type of the device 120. In this exemplary embodiment, device 120 includes a toroidal suction hood 121, which is integral to support base 131 and is configured to surround laterally support body 20. Toroidal hood 121 is then joined to a suction tube 122 arranged in turn to connect pneumatically the suction hood 121 with a suction system 123 that has a compressor to generate a suction flow and with a storage reservoir containing any surplus particles of the dispensed fluid substance.

Alternatively, in an exemplary embodiment not shown in the figures, device 120 is a blowing device including a compressor adapted to generate a blowing current for removing any surplus particles of the delivered fluid substance. This way, it is not necessary that the apparatus includes auxiliary handling unit 140, like the exemplary embodiment of FIG. 1, since the toroidal hood 121 surrounds laterally the support body 20, whichever is the position reached by handling unit 130.

Figure 3:
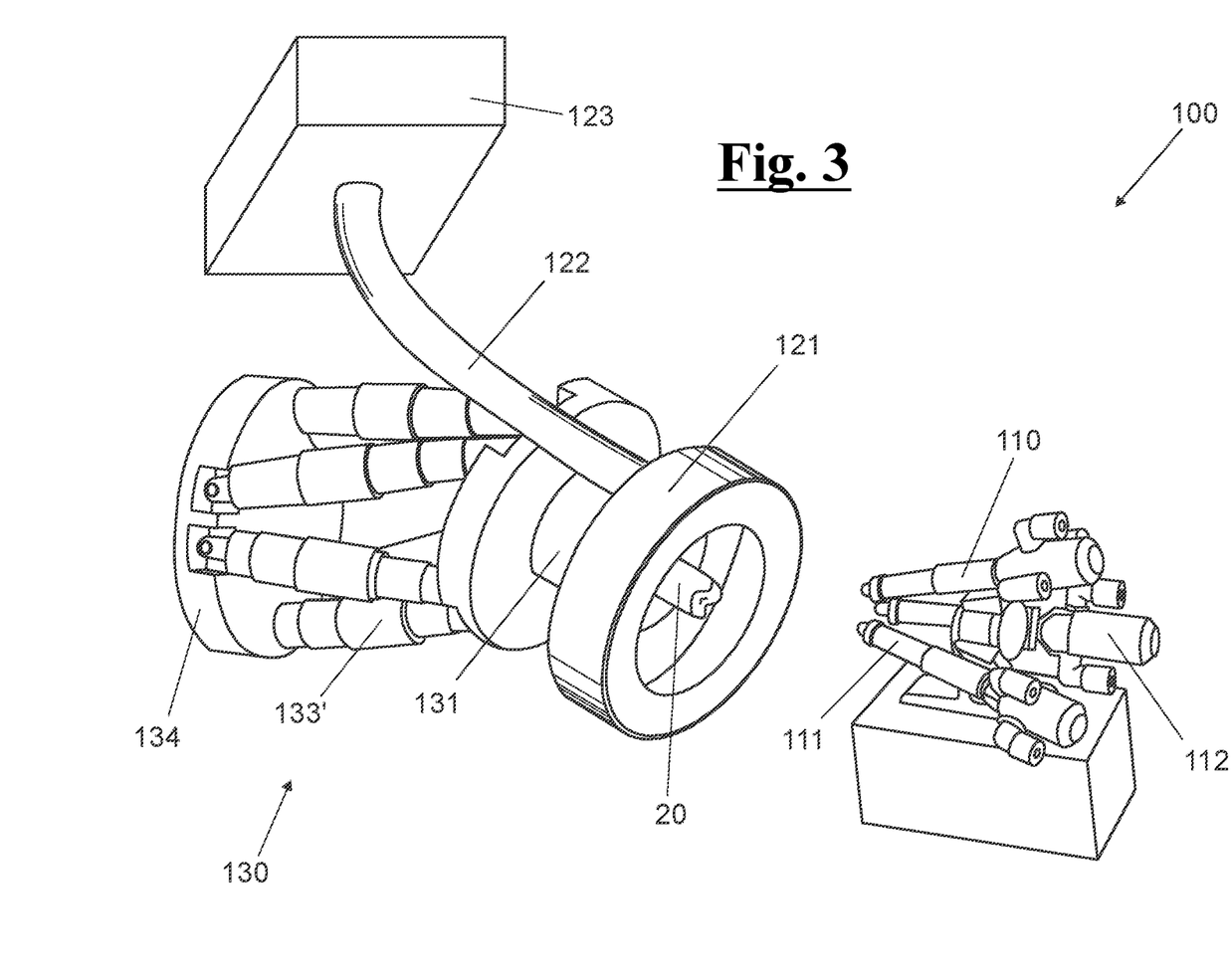
FIG. 3 shows an exemplary embodiment of the apparatus, which differs from that of FIG. 2 since the handling unit the support body does not include an anthropomorphic robot, but a plurality of linear actuators.

In FIG. 3 an exemplary embodiment is shown where handling unit 130, instead of including the anthropomorphic robot 132 of the previous figures, includes a plurality of linear actuators 133, each of which engages, at one end, to fixed base 134, and at another end, to support base 131. Support body 20 engages in a removable way with support base 131, like the previous exemplary embodiments. The handling unit can reach the same degrees of freedom of an anthropomorphic robot, even if with narrower handling range. The advantage offered by this solution is shown by a high reduction of the encumbrance.

Figure 4:
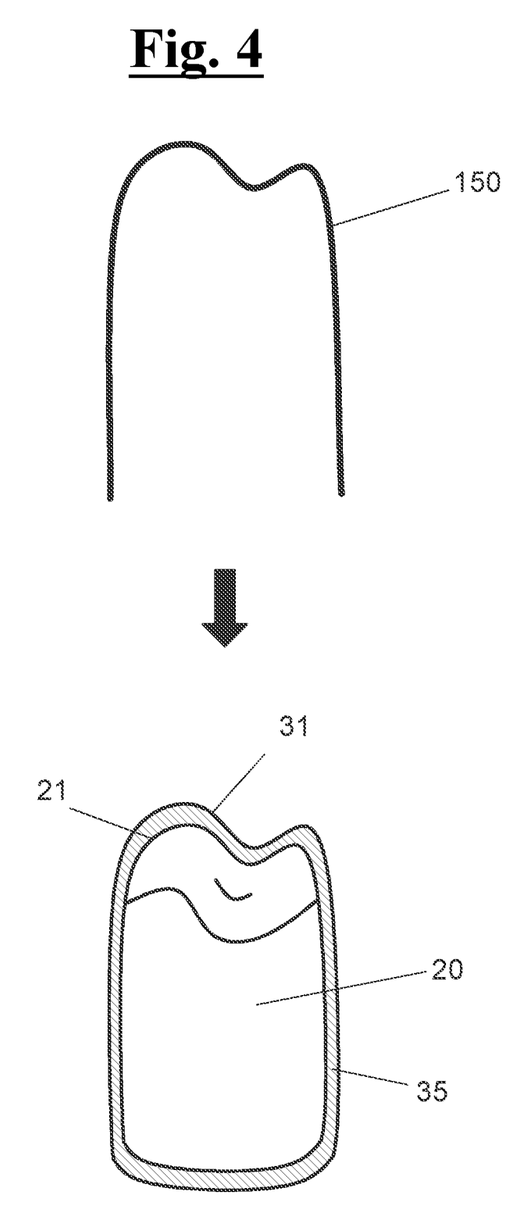
FIG. 4 shows a counter-mold that allows a hot molding of the coating layer.

In FIG. 4 the step is shown of pressing, in particular to hot pressing, of the coating layer 35 deposited by the or each delivery unit 110,111,112, using a counter-mold 150. The coating layer 35 is then removed from support body 20 and becomes substantially the final biocompatible three-dimensional object 30, visible in FIG. 5.

Figure 5:
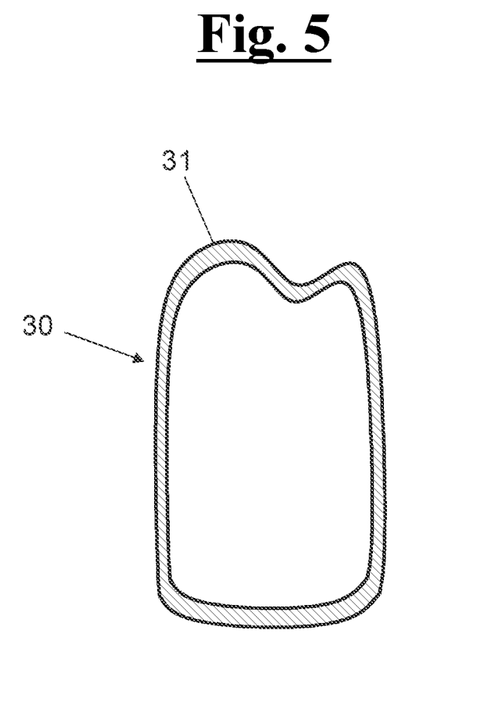
FIG. 5 shows a three-dimensional object resulting from the production process.

Owing to the hot pressing an optimum finishing of the shape of the three-dimensional object 30 can be achieved, in such a way that such shape is closest to the designed patch shape, for example provided by CAD or the like. Such pressing operation also gives to the three-dimensional object 30 mechanical improved features, reaching any design standards.

The apparatus 100, as described above, and shown in FIGS. 1 to 5, provides biocompatible three-dimensional objects 30 of whichever shape. In particular, biocompatible three-dimensional objects 30 can be manufactured both of simple and regular shape, such as a tetrahedron or a cone, and of irregular shape and/or with surfaces which cannot worked out in a simple way, such as a concave or convex patch or an ellipsoidal patch. Furthermore, biocompatible three-dimensional objects 30 can be provided having surfaces with different radius of curvature and/or with different angles.

Figure 6A:
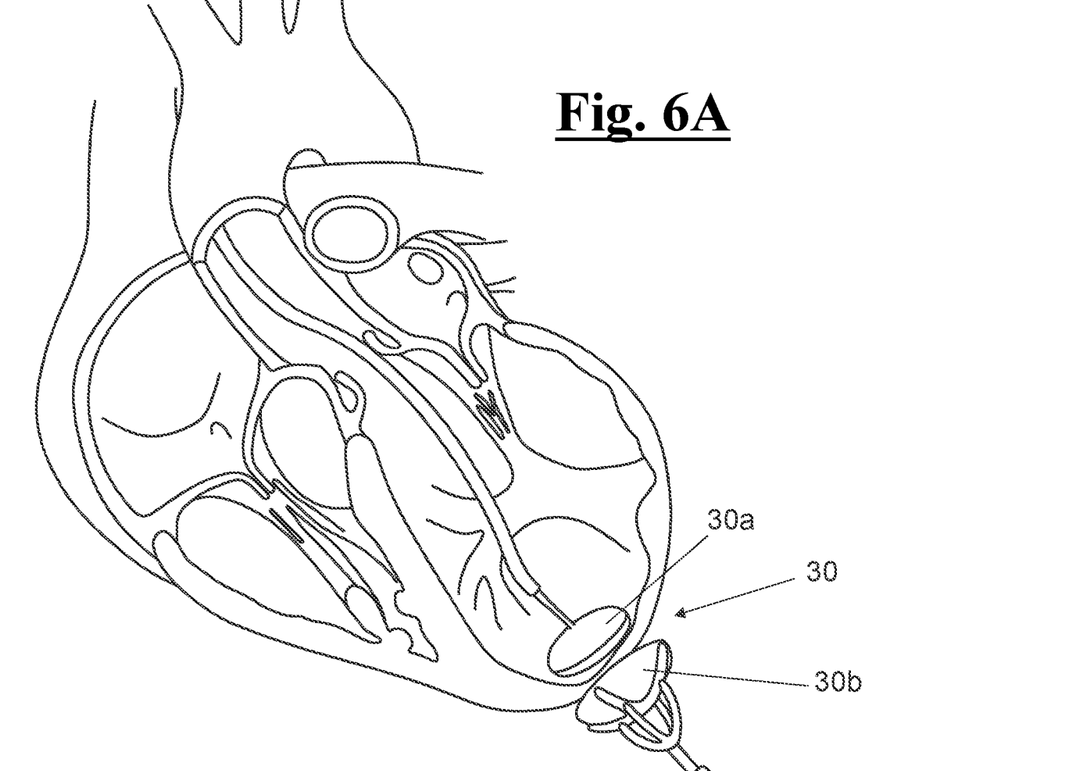
FIG. 6A shows a cardiac chamber with a heart patch applied to it.

In FIG. 6A a cardiac chamber of a human heart is shown to which a biocompatible three-dimensional object 30 is mounted, in particular a heart patch, consisting of an inner portion 30a and an external portion 30b.

Figure 6B:
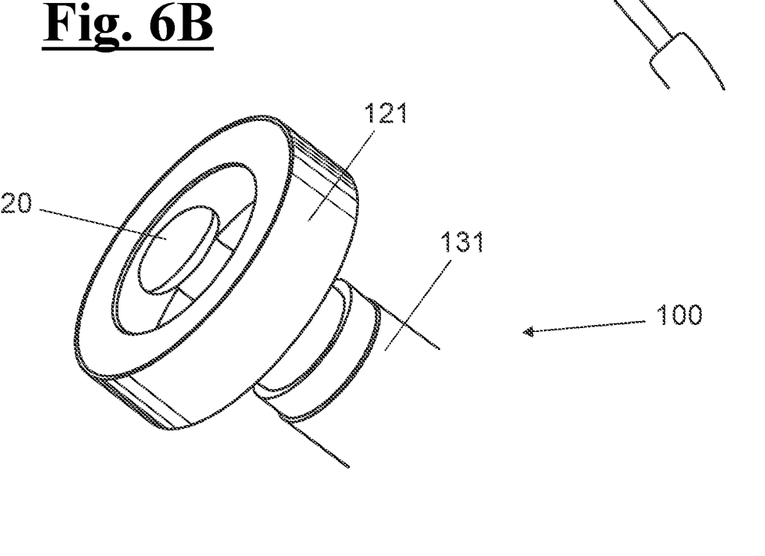
FIG. 6B shows a support from which the heart patch of FIG. 6A is generated.

In FIG. 6B part of the apparatus 100 including the support 20 is shown, from which the inner portion 30a of the heart patch of FIG. 6A is generated.

The foregoing description of specific exemplary embodiments will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realize the different functions described herein could have a different nature without, for this reason, departing from the field of the invention, it is to be understood that the phraseology or terminology that is employed herein is for the purpose of description and not of limitation.

The above described application relates to the MBP project "Fibrin-based nanostructured materials and platelet factors for stimulating angiogenesis" ("Materiali nanostrutturati a base di fibrina e fattori piastrinici in grado di promuovere 1' angiogenesi") admitted to R.T. financing, R&D Single Announcement, year 2008, 1.5-1.6 line B-Executive Decree 6744 of Dec. 31, 2008.

What is claimed:

1. An apparatus for making a biocompatible three-dimensional object, the apparatus comprising:
    a support body having a matrix surface with at least two radii of curvature;
    a handling unit supporting the support body;
    a delivery system arranged to deliver a biocompatible fluid substance having a plurality of particles towards the support body to obtain a coating layer of a predetermined thickness coating the matrix surface;
    a control unit arranged to monitor the thickness of the coating layer;
    a single suction and blowing device arranged to generate a suction or blowing current, the suction and blowing current configured to remove from the support body any surplus particles of the biocompatible fluid substance supplied by the delivery system; and
    a counter-mold that is adapted, once the delivery of the biocompatible fluid substance is completed, to press the coating layer deposited on the support body,
    wherein the handling unit is arranged to generate a relative movement with at least three degrees of freedom between the support body and the delivery system, in such a way that the support body can be coated with the delivered biocompatible fluid substance to obtain a three-dimensional object having an object surface corresponding to the matrix surface of the support body.

2. The apparatus of claim 1, wherein the handling unit includes an anthropomorphic robot having a chain of pivot joints, the chain of pivot joints having an end connected to a fixed base and the other end connected to a support base to which the support body or the delivery system can be removably mounted, the chain of pivot joints arranged to move the support body or the delivery system, according to at least six degrees of freedom.

3. The apparatus of claim 1, wherein the handling unit includes a plurality of linear actuators, each actuator of the plurality having an end engaged with a fixed base and another end engaged with a support base to which the support body or the delivery system is removably mounted.

4. The apparatus of claim 1, wherein the suction and blowing device is fixed.

5. The apparatus of claim 1, wherein the suction and blowing device is movable and associated with auxiliary moving means arranged to move the suction and blowing device, the auxiliary moving means being configured to allow the suction and blowing device to follow spatially the position of the support body during its handling by the handling unit.

6. The apparatus of claim 1, wherein the suction and blowing device includes a suction hood integral to the support base and configured to surround laterally the support body, in order to maximize the suction of the surplus particles of the biocompatible fluid substance, and a suction tube arranged to connect pneumatically the suction hood with a suction system.

7. The apparatus of claim 1, wherein the delivery system includes a first delivery unit arranged to deliver a first jet of the biocompatible fluid substance towards the support body, the biocompatible fluid substance being a biomaterial of synthetic origin, and a second delivery unit arranged to deliver a second jet of a second biocompatible fluid substance towards the support body, the second biocompatible fluid substance being a non-solvent, the second delivery unit arranged to direct the second jet towards the support body in such a way that the second jet overlaps the first jet, inducing a quick deposit of the synthetic biomaterial supplied onto the support body from the first delivery unit obtaining a filamentous three-dimensional structure.

8. The apparatus of claim 7, wherein the second biocompatible fluid substance is water.

9. The apparatus of claim 7, wherein the delivery system includes a third delivery unit arranged to deliver a third biocompatible fluid substance.

10. The apparatus of claim 9, wherein the third biocompatible fluid substance is a biopolymeric material of synthetic origin.

11. The apparatus of claim 1, wherein the thickness of the coating layer is capable of being adjusted.

* * * * *